US00PP24307P2

(12) United States Plant Patent
Beekenkamp

(10) Patent No.: US PP24,307 P2
(45) Date of Patent: Mar. 11, 2014

(54) ***BEGONIA* PLANT NAMED 'BKPBECVP'**

(50) Latin Name: *Begonia hiemalis*
Varietal Denomination: BKPBECVP

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 12 days.

(21) Appl. No.: 13/507,635

(22) Filed: Jul. 13, 2012

(51) Int. Cl.
*A01H 5/00* (2006.01)

(52) U.S. Cl.
USPC ..... Plt./348

(58) Field of Classification Search
USPC ..... Plt./348
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'BKPBECVP', characterized by its broadly upright, somewhat outwardly spreading and mounded plant habit; moderately freely basal branching habit; medium-size leaves; uniform and freely flowering habit; and flowers that are light pink in color on both the upper and lower surfaces.

2 Drawing Sheets

Botanical designation: *Begonia hiemalis*.
Cultivar denomination: 'BKPBECVP'.

BACKGROUND OF THE INVENTION

The present invention relates to a new and distinct cultivar of *Begonia* plant, botanically known as *Begonia hiemalis*, commercially referred to as a Elatior *Begonia* and hereinafter referred to by the name 'BKPBECVP'.

The new *Begonia* plant is a product of a planned breeding program conducted by the Inventor in Amstelveen, The Netherlands. The objective of the breeding program was to develop new freely branching and freely flowering *Begonia* plants with attractive foliage and flower colors.

The new *Begonia* plant originated from a cross-pollination made by the Inventor in September, 2006 of a proprietary selection of *Begonia hiemalis* identified as code number 06-187-01, not patented, as the female, or seed, parent with a proprietary selection of *Begonia hiemalis* identified as code number 6500604, not patented, as the male, or pollen, parent. The new *Begonia* plant was discovered and selected by the Inventor as a single flowering plant from within the progeny of the stated cross-pollination in a controlled greenhouse environment in Amstelveen, The Netherlands in October, 2007.

Asexual reproduction of the new *Begonia* plant by tip cuttings in a controlled greenhouse environment in Amstelveen, The Netherlands since February, 2008 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBECVP'.

These characteristics in combination distinguish 'BKPBECVP' as a new and distinct *Begonia* plant:

1. Broadly upright, somewhat outwardly spreading and mounded plant habit.
2. Moderately freely basal branching habit.
3. Medium-size leaves.
4. Uniform and freely flowering habit.
5. Flowers that are light pink in color on both the upper and lower surfaces.

Plants of the new *Begonia* can be compared to plants of the female parent selection. Plants of the new *Begonia* differ primarily from plants of the female parent selection primarily in the following characteristics:

1. Leaves of plants of the new *Begonia* are lighter green in color than leaves of plants of the female parent selection.
2. Leaves of plants of the new *Begonia* are glabrous whereas leaves of plants of the female parent selection are slightly pubescent.
3. Plants of the new *Begonia* have smaller flowers than plants of the female parent selection.

Plants of the new *Begonia* can be compared to plants of the male parent selection. Plants of the new *Begonia* differ primarily from plants of the male parent selection in the following characteristics:

1. Plants of the new *Begonia* have larger flowers than plants of the male parent selection.
2. Plants of the new *Begonia* and the male parent selection differ slightly in flower color as plants of the male parent selection have pale pink-colored flowers.

Plants of the new *Begonia* can be compared to plants of the *Begonia* 'Nelly', not patented. In side-by-side comparisons conducted in Amstelveen, The Netherlands, plants of the new *Begonia* differed from plants of 'Nelly' in the following characteristics:

1. Plants of the new *Begonia* were more upright than plants of 'Nelly'.
2. Plants of the new *Begonia* were not as compact as plants of 'Nelly'.

3. Plants of the new *Begonia* and 'Nelly' differed slightly in flower color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBECVP' grown in a container.

The photograph on the second sheet is a close up view of the upper and lower surfaces of typical flower buds, flowers and leaves of 'BKPBECVP'.

DETAILED BOTANICAL DESCRIPTION

Plants used for the aforementioned photographs and following observations and measurements were grown in 12-cm containers during the winter in a glass-covered greenhouse in Maasdijk, The Netherlands. During the production of the plants, day and night temperatures ranged from 18° C. to 19° C. and light levels averaged 7,000 lux. Plants were twelve weeks old when the photographs and the description were taken. In the following description, color references are made to The Royal Horticultural Society Colour Chart, 2007 Edition, except where general terms of ordinary dictionary significance are used.

Botanical classification: *Begonia hiemalis* 'BKPBECVP'.

Parentage:

*Female, or seed, parent*.—Proprietary selection of *Begonia hiemalis* identified as code number 06-187-01, not patented.

*Male, or pollen, parent*.—Proprietary selection of *Begonia hiemalis* identified as code number 6500604, not patented.

Propagation:

*Type*.—By tip cuttings.

*Time to initiate roots, summer and winter*.—About 20 days at temperatures of about 25° C.

*Time to produce a rooted young plant, summer and winter*.—About 35 to 36 days at temperatures of about 21° C. to 23° C.

*Root description*.—Medium in thickness, fibrous; white in color; plants of the new *Begonia* have not been observed to form tubers.

*Rooting habit*.—Moderate branching; medium density.

Plant description:

*Plant form and growth habit*.—Broadly upright, somewhat outwardly spreading and mounded plant habit; plant shape roughly globular; moderately freely basal branching with about five basal branches per plant; moderately vigorous growth habit.

*Plant height*.—About 22.3 cm.

*Plant width*.—About 26.6 cm.

*Branch description*.—Length: About 12.2 cm. Diameter: About 8 mm. Internode length: About 2.2 cm. Texture: Sparsely pubescent. Aspect: Upright to about 30° from vertical. Color, developing: Close to 144A. Color, fully developed: Close to 144A to 144B.

*Leaf description*.—Arrangement: Alternate, simple. Length: About 12.2 cm. Width: About 8.7 cm. Shape: Broadly ovate. Apex: Obtuse. Base: Oblique to hastate. Margin: Bi-crenate. Texture, upper and lower surfaces: Smooth, glabrous; velvety. Venation pattern: Palmate; reticulate. Color: Developing leaves, upper surface: Close to 146A. Developing leaves, lower surface: Close to 148A to 148B. Fully expanded leaves, upper surface: Darker than between N137A and 147A; venation, close to 144A. Fully expanded leaves, lower surface: Close to 191B to 191C slightly tinged with close to 176B; venation, close to 146C. Petioles: Length: About 7.9 cm. Diameter: About 5 mm. Texture, upper and lower surfaces: Sparsely pubescent. Color, upper surface: Close to 145A; distally, slightly tinged with close to 180A to 180B. Color, lower surface: Close to 145A.

Flower description:

*Flowering habit*.—Female and sterile male rotate flowers arranged in axillary compound cymes; freely flowering habit with about five flowers per cyme and about 100 flowers developing per plant; flowers face upright to outwardly.

*Fragrance*.—None detected.

*Natural flowering season*.—Plants begin flowering about ten weeks after planting; long flowering period, plants flower freely and continuously from spring until autumn in The Netherlands.

*Flower longevity*.—Individual flowers last about ten days on the plant; flowers not persistent.

*Inflorescence height*.—About 16.6 cm.

*Inflorescence diameter*.—About 11.5 cm.

*Female flowers*.—Diameter: About 3.7 cm. Height: About 2.3 cm. Flower buds: Length: About 2.1 cm. Diameter: About 2.1 cm. Shape, flattened: Orbicular. Color: Close to 174B to 174C; towards the base, close to 144C. Tepals: Quantity per flower and arrangement: About five in a single whorl. Length: About 2.2 cm. Width: About 2.5 cm. Shape: Reniform. Apex: Rounded. Margin: Entire. Texture, upper surface: Smooth, glabrous; slightly velvety. Texture, lower surface: Smooth, glabrous; moderately velvety. Color: When opening, upper surface: Close to 65D; towards the base, close to 145B to 145C. When opening, lower surface: Between 173C and 174C; towards the base, close to 144C. Fully opened, upper surface: Between 65C and 69A; towards the base, close to 145B to 145C; color does not change with development. Fully opened, lower surface: Close to 180C; towards the base, close to 174B to 174C; color does not change with development.

*Male flowers*.—Diameter: About 5.6 cm. Height: About 2.4 cm. Flower buds: Length: About 1.7 cm. Diameter, flattened: About 1.9 cm. Shape, flattened: Reniform. Color: Close to 174B to 174C; towards the base, close to 144C. Tepals: Quantity per flower and arrangement: About four in a single whorl. Length: About 3.1 cm. Width: About 3.6 cm. Shape: Reniform. Apex: Rounded. Margin: Entire. Texture, upper surface: Smooth, glabrous; slightly velvety. Texture, lower surface: Smooth, glabrous; moderately velvety. Color: When opening, upper surface: Close to 150D; towards the margins, tinged with close to 65B to 65C. When opening, lower surface: Close to 150D; towards the margins, tinged with close to 181D. Fully opened, upper surface: Close to 181D to lighter than 181D; towards the base, strongly tinged with close to 146D;

color does not change with development. Fully opened, lower surface: Close to 145A; towards the margins, tinged with close to 181D to lighter than 181D; color does not change with development.

*Tepaloids*.—Tepaloid development has been observed only on male flowers of the new *Begonia* plant. Quantity per flower and arrangement: About 14 in several whorls. Length: About 2.4 cm. Width: About 1.9 cm. Shape: Obovate. Apex: Obtuse. Margin: Entire. Texture, upper surface: Smooth, glabrous; slightly velvety. Texture, lower surface: Smooth, glabrous; moderately velvety. Color: When opening, upper and lower surfaces: Close to 65C; towards the base, tinged with close to 145D. Fully opened, upper surface: Close to 65D; towards the base, tinged with close to 145D; color does not change with development. Fully opened, lower surface: Close to 65C; towards the base, tinged with close to 145D; color does not change with development.

*Peduncles*.—Length: About 7.8 cm. Diameter: About 4 mm. Angle: About 30° from branch axis. Texture: Smooth, glabrous. Color: Close to 144A.

*Pedicels*.—Length: About 4 cm. Diameter: About 2 mm. Angle: About 35° from the peduncle axis. Texture: Smooth, glabrous. Color, female flowers: Close to 173A. Color, male flowers: Between 152A and 199A.

*Reproductive organs*.—Stamens: Stamen development has not been observed on male flowers of plants of the new *Begonia*. Pistils: Present only on female flowers. Quantity per flower: About six. Length: About 5 mm. Style length: About 2 mm. Style color: Close to 144C. Stigma color: Close to 15A. Ovary color: Close to 144A strongly tinged with close to 174B.

*Seeds and fruits*.—Seed and fruit development production has not been observed on plants of the new *Begonia*.

Disease & pest resistance: Resistance to pathogens and pests common to *Begonia* has not been observed on plants of the new *Begonia*.

Temperature tolerance: Plants of the new *Begonia* have been observed to tolerate temperatures from about 14° C. to about 35° C.

It is claimed:

1. A new and distinct *Begonia* plant named 'BKPBECVP' as illustrated and described.

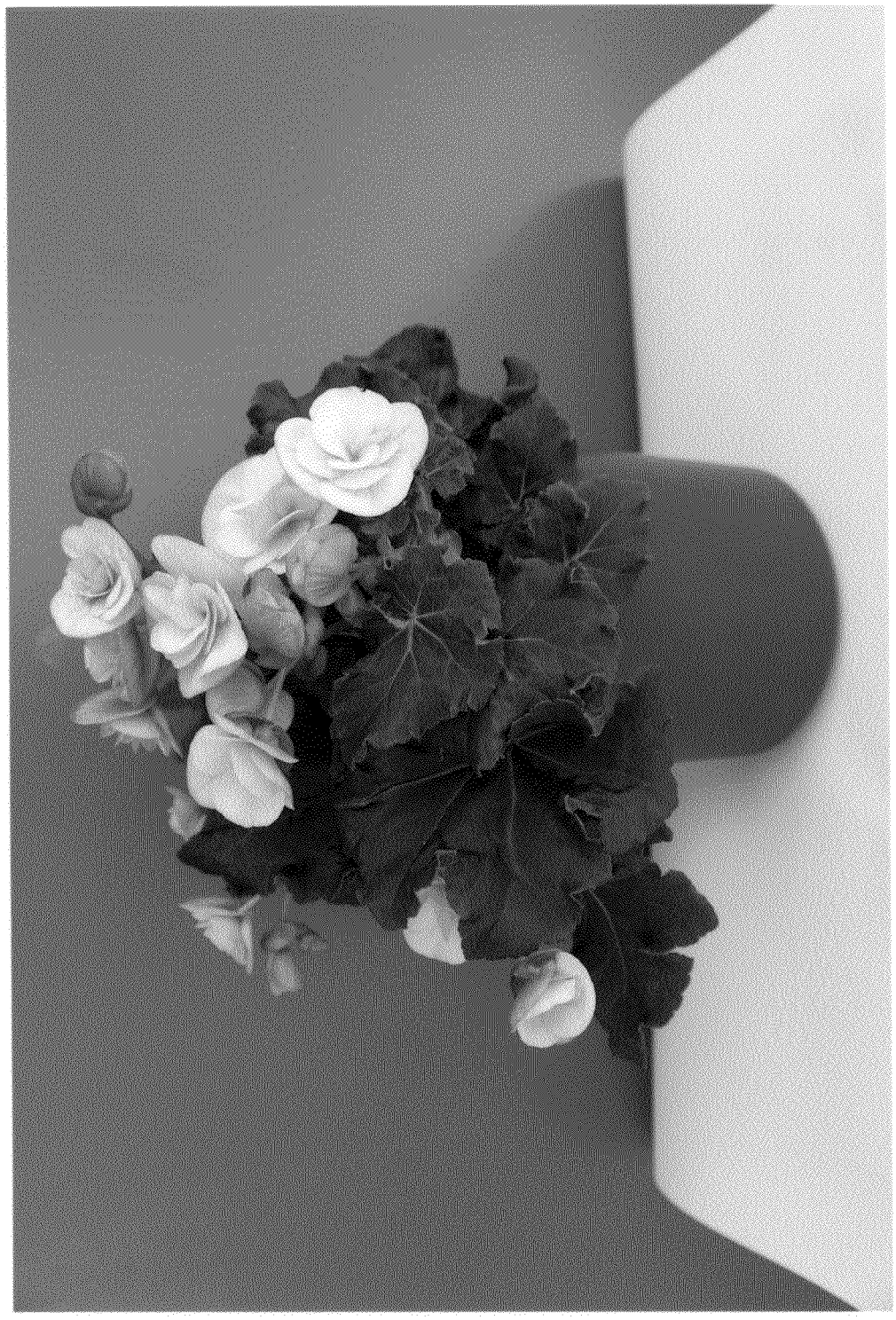

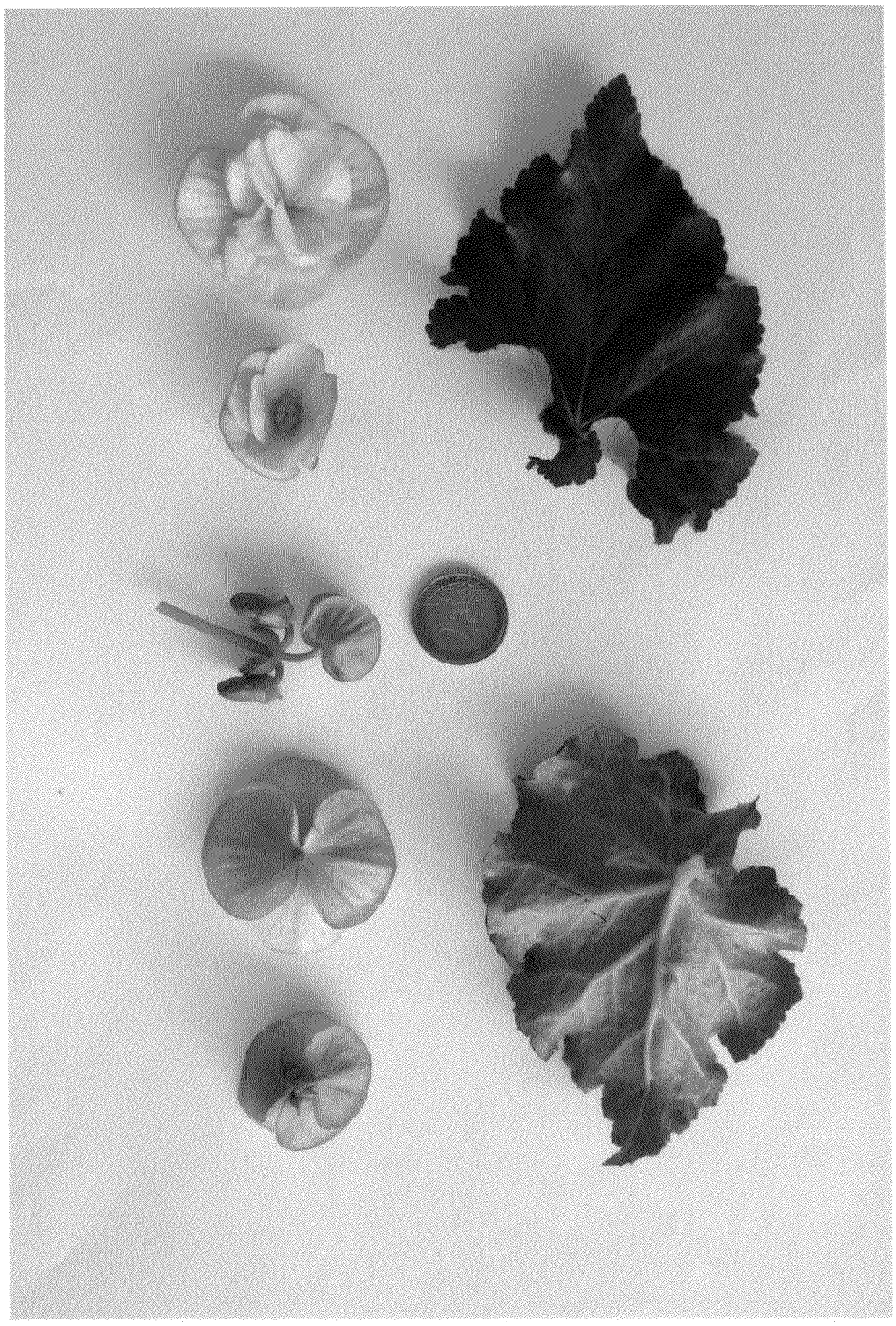

* * * * *